United States Patent
De Sapio et al.

(10) Patent No.: US 10,052,062 B2
(45) Date of Patent: Aug. 21, 2018

(54) SYSTEM AND METHOD FOR ASSISTIVE GAIT INTERVENTION AND FALL PREVENTION

(71) Applicant: HRL Laboratories, LLC, Malibu, CA (US)

(72) Inventors: Vincent De Sapio, Westlake Village, CA (US); Michael D. Howard, Westlake Village, CA (US); Suhas E. Chelian, San Jose, CA (US); Matthias Ziegler, Oakton, VA (US); Matthew E. Phillips, Calabasas, CA (US); Kevin R. Martin, Oak Park, CA (US); Heiko Hoffmann, Simi Valley, CA (US); David W. Payton, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/042,078

(22) Filed: Feb. 11, 2016

(65) Prior Publication Data
US 2017/0303849 A1     Oct. 26, 2017

Related U.S. Application Data

(60) Provisional application No. 62/115,495, filed on Feb. 12, 2015.

(51) Int. Cl.
*A61B 5/00* (2006.01)
*A61B 5/11* (2006.01)
(Continued)

(52) U.S. Cl.
CPC .......... *A61B 5/4836* (2013.01); *A61B 5/0488* (2013.01); *A61B 5/112* (2013.01);
(Continued)

(58) Field of Classification Search
CPC ... A61B 5/4836; A61B 5/0488; A61B 5/1117; A61B 5/112
See application file for complete search history.

(56) References Cited

U.S. PATENT DOCUMENTS

| 8,092,398 B2 | 1/2012 | Weinberg et al. |
| 2007/0208392 A1 | 9/2007 | Kuschner et al. |

(Continued)

FOREIGN PATENT DOCUMENTS

| WO | 2014-134564 | 9/2014 |

OTHER PUBLICATIONS

L R. Bent; B. J. McFadyen, V. French Merkley, P. M. Kennedy, and J. T. Inglis, "Magnitude effects of galvanic vestibular stimulation on the trajectory of human gait," Neuroscience letters, 279 (3), pp. 157-160, 2000.

(Continued)

*Primary Examiner* — Joseph Dietrich
(74) *Attorney, Agent, or Firm* — Tope-McKay & Associates

(57) ABSTRACT

Described is a system for system for gait intervention and fall prevention. The system is incorporated into a body suit having a plurality of distributed sensors and a vestibulo-muscular biostim array. The sensors are operable for providing biosensor data to the analytics module, while the vestibulo-muscular biostim array includes a plurality of distributed effectors. The analytics module is connected with the body suit and sensors and is operable for receiving biosensor data and analyzing a particular user's gait and predicting falls. Finally, a closed-loop biostim control module is included for activating the vestibulo-muscular biostim array to compensate for a risk of a predicted fall.

17 Claims, 11 Drawing Sheets

(51) Int. Cl.
A61B 5/0488 (2006.01)
A61N 1/36 (2006.01)
(52) U.S. Cl.
CPC .......... *A61B 5/1117* (2013.01); *A61B 5/4023* (2013.01); *A61B 5/6804* (2013.01); *A61B 5/7275* (2013.01); *A61B 5/746* (2013.01); *A61N 1/36003* (2013.01)

(56) References Cited

U.S. PATENT DOCUMENTS

2010/0049096 A1  2/2010  Warner et al.
2011/0152727 A1  6/2011  Warner et al.

OTHER PUBLICATIONS

C. Boelens, E. E. G. Hekman, and G. J. Verkerke, "Risk factors for falls of older citizens," Technology and Heaith Care pp. 1-13, 2013. doi: 10.3233/THC-130748. URL http//iospress.metapress.com/content/9180L23KHL7486R0.
A. K. Bourke and G. M. Lyons, "A threshold-based fall-detection algorithm using a bi-axial gyroscope sensor" Medical engineering & physics: 30 (1), pp. 84-90, 2008.
V. De Sapio, "An approach for goal-oriented neuromuscular control of digital humans in physics-based simulations," International Journal in Human Factors Modeling and Simulation, 2013. In review, pp. 121-144.
V. De Sapio, J. Warren, O. Khatib, and S. Delp, "Simulating the task-level control of human motion: a methodology and framework for implementation" The Visual Computer; 21 (5), pp. 289-302, 2005.
V. De Sapio, J. Warren, and O. Khatib, "Predicting reaching postures using a kinematically constrained shoulder model," In Advances in robot kinematics, pp. 209-218, Springer, 2006.
S. L. Delp, F. C. Anderson, A. S. Arnold, P. Loan, A. Habib, C. T. John, E. Guendelman, and D. G. Thelen, "OpenSim: open-source software to create and analyze dynamic simulations of movement," IEEE Transactions on Biomedical Engineering, 54 (11), pp. 1940-1950, 2007.
F. Englander, T. J. Hodson, and R. A. Terregrossa, "Economic dimensions of slip and fall injuries," Journal of forensic sciences, 41 (5), pp. 733-746, 1996.
J. Fleming and C. Brayne, "Inability to get up after falling, subsequent time on floor, and summoning help: prospective cohort study in people over 90," BMJ: British Medical Journal, 337, 2008, pp. 1-8.
H. Geyer and H. Herr, "A muscle-reflex model that encodes principles of legged mechanics produces human walking dynamics and muscle activities," IEEE Transactions on Neural Systems and Rehabilitation Engineering, 18 (3) pp. 263-273, 2010.
M. Giftthaler and K. Byl, "Increased robustness of humanoid standing balance in the sagittal plane through adaptive joint torque reduction," In Proceedings of the 2013 IEEE International Conference on Intelligent Robots and Systems, 2013, pp. 4130-4136.
M. H. Granat, A. C. B. Ferguson, B. J. Andrews, and M. Delargy, "The role of functional electrical stimulation in the rehabilitation of patients with incomplete spinal cord injury-observed benefits during gait studies," Spinal Cord, 31 (4), pp. 207-215, 1993.
E. E. Hansson and M. Magnusson, "Vestibular asymmetry predicts fails among elderly patients with multi-sensory dizziness," BMC geriatrics, 13 (1), pp. 77-82, 2013.
B. Kleiner and D. Cesmeci, "D8. 4-foresighted control of active foot prostheses," Proceedings SENSOR 2011, pp. 669-672, 2011.
A.. D. Kuo, "An optimal control model for analyzing human postural balance," IEEE Transactions on Biomedical Engineering, 42 (1), pp. 87-101, 1995.
C. Liu and C. G. Atkeson, "Standing balance control using a trajectory library," In Proceedings of the 2009 IEEE/RSJ International Conference on Intelligent Robots and Systems, pp. 3031-3036. IEEE, 2009.

M. Malešvic and S. Hesse, "Restoration of gait by functional electrical stimulation in paraplegic patients: a modified programme of treatment," Spinal Cord, 33 (3), pp. 126-131, 1995.
M. Mansouri and J. A. Reinbolt, "A platform for dynamic simulation and control of movement based on OpenSim and MATLAB," Journal of biomeohanics, 45 (8). pp. 1517-1521, 2012.
K. Miller, "Feedback for the brain and body: A new freely available interface between matlab and opensim," Biomedical Computation Review, Summer: pp. 3-4, 2012.
A. Murai and K. Yamane, "A neuromuscular locomotion controller that realizes human-like responses to unexpected disturbances," In 2011 IEEE International Conference Robotics and Automation. pp. 1997-2002. IEEE, 2011.
S. Piazza, M. Mansouri, D. Torricelli, J. A. Reinbolt, and J. L. Pons, "A biomechanical model for the validation of modular control in balance," In Converging Clinical and Engineering Research on Neurorehabilitation, pp. 815-819. Springer, 2013.
J. Piovan and K. Byl, "Reachability-based control for the active slip model," International Journal of Robotics Research, page Submitted, 2013, pp. 270-287.
J. Pratt, J. Carff, S. Drakunov, and Am. Goswami, "Capture point: A step toward humanoid push recovery," in 2006 6th IEEE-RAS international Conference on Humanoid Robots, pp. 200-207. IEEE, 2006.
X. Qu. "Effects of cognitive and physical loads on local dynamo stability during gait," Applied Ergonomics, 44 (3), pp. 455-458, 2013. ISSN 0003-6870. doi: http://dx.doi.org/10.1016/j.apergo.2012.10.018. URL http://www.sciencedirect.com/sciencearticle/pii/S0003687012001767.
X Qu and J. C. Yeo, "Effects of load carriage and fatigue on gait characteristics," Journal of biomechanics, 44 (7), pp. 1259-1263, 2011.
M. Raibert, K. Blankespoor, G. Nelson, R. Playter, et al., "Bigdog, the rough-terrain quadruped robot," In Proceedings of the 17th World Congress of the International Federation of Automatic Control, pp. 10823-10825, 2008.
J. A. Reinbolt, R. T. Haftka, T. L Chmielewski, and B. J. Fregly, "Are patient-specific joint and inertial parameters necessary for accurate inverse dynamics analyses of gait?" IEEE Transactions on Biomedical Engineering, 54 (5), pp. 782-793, 2007.
C. O. Saglam and K. Byl, "Switching policies for metastable walking," In In Proceedings of IEEE Conference on Decision and Control, 2013, pp. 977-983.
M. Sartori, D. G. Lloyd, M. Reggiani, and E. Pagello, "A stiff tendon neuromusckletetal model of the knee," In 2009 IEEE Workshop on Advanced Robotics and its Social Impacts, pp. 132-138. IEEE, 2009.
M Sartori, D. G. Lloyd, M. Reggiani, and E. Pagello, "Fast operation of anatomical and stiff tendon neuromuscular models in emg-driven modeling," In 2010 IEEE international Conference on Robotics and Automation, pp. 2228-2234. IEEE, 2010.
M. Sartori, M. Reggiani, D. Farina, and D. G. Lloyd, "Emg-driven forward-dynamic estimation of muscle force and joint moment about multiple degrees of freedom in the human lower extremity," PloS one, 7 (12): e52618, 2012.
A. P. Scinicariello, K. Eaton, J. T. Inglis, and J. J. Collins, "Enhancing human balance control with galvanic vestibular stimulation," Biological cybernetics, 84 (6), pp. 475-480, 2001.
L. Senier, N. S. Bell, M. M. Yore, and P. J. Amoroso, "Hospitalizations for fall-related injuries among active-duty army soldiers, 1980-1998." Work: A Journal of Prevention, Assessment and Rehabilitation, 18 (2), pp. 161-170, 2002.
A. Seth, M. Sherman, J. A. Reinbolt, and S. L. Delp, "OpenSim: a musculoskeletai modeling and simulation framework for in silica investigations and exchange," vol. 2, pp. 212-232. Elsevier, 2011.
E. Shuping, M. Canham-Chervak, P. J. Amoroso, and B. H. Jones, "Identifying modile causes of fall-related injury an analysis of us army safety data," Work: A Journal of Prevention, Assessment and Rehabiiitation, 33 (1), pp. 23-34, 2009.
Yousuke Suzuki, Takayuki Tanaka, Shun'ichi Kaneko, Shunji Moromugi, and Maria Q Feng. "Soft sensor suits as man-machine

(56) References Cited

OTHER PUBLICATIONS interface for wearable power ampilfier," In Systems, Man and Cybernetics, 2005 IEEE International Conference on, vol. 2, pp. 1680-1685. IEEE, 2005.

W. Tao, T, Liu, R. Zheng, and H. Feng, "Gait analysis using wearable sensors,". Sensors. 12 (2), pp. 2255-2283, 2012.

D. G. Thelen and F. C. Anderson, "Using computed muscle control to generate forward dynamic simulations of human walking from experimental data" Journal of Biomechanics. 39 (6), pp. 1107-1115, 2006.

D. G. Thelen, F. C. Anderson, and S. L. Delp, "Generating dynamic simulations of movement using computed muscle control," Journal of Biomechanics. 36 (3), pp. 321-328, 2003.

M. Van Diest, C. J. C. Lamoth, J. Stegenga, G. J. Verkerke, and K. Postema, "Exergaming for balance training of elderly: state of the art and future developments," Journal of neuroengineering and rehabilitation, 10 (1), pp. 101-112, 2013.

R. van Swigchem, et al., "Is transcutaneous peroneal stimulation beneficial to patients with chronic stroke using an ankle-foot orthosis? A within-subjects study of patients' satisfaction, walking speed and physical activity level," Journal of Rehabilitation Medicine, 42 (2), pp. 117-121, 2010.

Q. Zhang, M. Hayashibe, and C. Azevedo-Coste, "Evoked electromyography-based closed-loop torque control in functional electrical stimulation," IEEE Transactions on Biomedical Engineering, 60, pp. 2299-2307, 2013.

Y. Zigel, D. Litvak, and I. Gannot, "A method for automatic fall detection of elderly people using floor vibrations and sound-proof of concept on mimicking doll falls," IEEE Transactions on Biomedical Engineering, 56 (12), pp. 2858-2867, 2009.

International Search Report of the International Searching Authority for PCT/US2016/017643; dated May 25, 2016.

The Written Opinion of the International Searching Authority for PCT/US2016/017643; dated May 25, 2016.

Notification of Transmittal of International Search Report and the Written Opinion of the International Searching Authority for PCT/US2016/017643; dated May 25, 2016.

Notification Concerning Transmittal of International Preliminary Report on Patentability for PCT/US2016/017643; dated Aug. 24, 2017.

International Preliminary Report on Patentability for PCT/US2016/017643; dated Aug. 24, 2017.

| | Item | Description | Prototype | | | Purpose | Performance |
|---|---|---|---|---|---|---|---|
| | | | Size mm | Weight | Power | | |
| Body Units | 2 Haptic actuators | Vibration motor | 10x10x 2.7 | 5g | 270mW | Provides haptic feedback for imminent falls | 9000 RPM |
| | 50 Combined EMG/FES electrodes + 1 control unit | EMG sensors with FES electrodes | 15x15x5 ea+ 81x46x23 | 5g ea + 113g unit | 18 mW ea + 7.2 W unit | Monitor muscle activity and stimulate muscles | 500-1000kHz sample rate; Muscle contracts 40% if unaided, or 80% if user helps |
| | 10 Inertial Measurement Units | YEI Tech 3Space Sensors (triaxial gyro, accelerometer, compass) | 23x23x 2.2 | 1.3g ea | 225mW ea unit | Monitor positions of left and right hallux (big toe), ankle, knee and hip joints. | <0.08° orientation, 0.00048g/digit ±4g range accelerometer |
| Head | 2 GVS control units | Galvanic Vestibular Stimulation. 1 pair of electrodes per unit. | 178x127x38 | 510g per unit | 15 mW | Actuate vestibular response in user | Reflex: 56ms short, 105ms middle-latency |

FIG. 5B

|  | Item | Description | Prototype ||| Purpose | Performance |
|--|------|-------------|------|--------|-------|---------|-------------|
|  |  |  | Size mm | Weight | Power |  |  |
| Leg | 2 GRF | Ground Reactive Force (insoles in shoes) | ~300x80x10 | ~60g ea | 12.5mW | Measure foot loading |  |
|  | 2 Environ-mental Range Sensors | Micro Laser Range Finder mounted on feet (e.g.) | 102x54x26 | 90g ea | Max 3W | Measure ground contour ahead | 1mm accuracy,100Hz sample rate, range 2.5-8m |
|  | Regenerative power insole | Recharges battery from foot strike forces | ~300x80x20 | ~300g ea | -- | Sustains longer operation | Generates 1500 mW/mile |
| Misc. | 2 Processors | Single Board Computers | 76x76x16 | 40g | 6-10W | Off board, Ph2: On-board | ARM Cortex-A8 1GHz |
|  | Body Area Network | IEEE standard 802.15.4 | Part of sensors |  |  | Sensor mesh network for collecting data | 250kbps per sensor channel |
|  | Local Area Network | IEEE standard 802.11 | Off-board |  |  | Ph1: Relaying coalesced sensor data to processor | 4-5Mbps |
|  | 1 Battery | Li-ion | 185x66x19 | 530g | 80 W-hrs | Soft suit power | ~1-2 hr operation |
|  | Suit or straps | Soft, durable material | -- | 360g | -- | Holds sensors, actuators, and processors | Conformal and light |

FIG. 5C

SYSTEM AND METHOD FOR ASSISTIVE GAIT INTERVENTION AND FALL PREVENTION

CROSS-REFERENCE TO RELATED APPLICATIONS

This is a non-provisional patent application of U.S. Provisional Application No. 62/115,495, filed on Feb. 12, 2015, the entirety of which is hereby incorporated by reference.

BACKGROUND OF INVENTION

(1) Field of Invention

The present invention is related to a fall prevention system and, more particularly, to a system incorporating a suit and sensors to predict impending falls by a user and initiate protocols to engage in the prevention of such a fall.

(2) Description of Related Art

Falls are a significant cause of hospitalizations among active duty soldiers (see the List of Incorporated Literature References, Literature Reference Nos. 33 and 35) as well as among the elderly. For example, 1 in 3 people over the age of 65 will experience a debilitating fall each year, with direct health care costs estimated at over $30 Billion per year (see Literature Reference No. 8). Both load (e.g., backpack weight) and fatigue increase the danger of fall accidents (see Literature Reference Nos. 24 and 25).

To mitigate the risk of falls, there is a need for a system that is operable for protecting a user from the injuries associated with such a fall. The state of the art, for example, detects falls by means of accelerometers, and uses stiff, weight-bearing exoskeletons to stop a fall. A problem with exoskeletons is that they are uncomfortable, bulky, and expensive. Further, such exoskeletons are awkward and they impede the mobility of the wearer if they run out of power. With such a bulky, stiff exoskeleton, prior art solutions can afford to wait until a fall is happening and then detect it and use the stiff exoskeleton to stop it.

The prior art also suffers from its sensing capabilities. To sense the user's gait, coarse body configuration data such as strike foot timing can only be applied to certain gait pathologies, such as drop foot (see Literature Reference No. 42). Further, to sense falls, gyroscopic sensors (see Literature Reference No. 3) are employed in the exoskeleton (which detect but do not predict). Non-wearable video motion capture systems are sometimes employed (see Literature Reference No. 44), which reduce the mobility of such systems. Other systems employ unreliable self-reporting (see Literature Reference No. 9), which can only detect and not predict falls. Further, such systems do not actively monitor extrinsic fail predictors, such as tripping hazards (see Literature Reference No. 2).

Other limitations exist in the prior art with respect to the ability to infer and predict biomechanical states. For example, generic biomechanical models for gait analytics are unlikely to capture the range of inertial properties from a tall, muscular soldier to a short, geriatric patient. Prior art in inferring muscle activations for musculoskeletal dynamics simulations is OpenSim (see Literature Reference No. 7) and CMC (see Literature Reference Nos. 38 and 39), respectively. Although accurate, these models are too computationally intensive to run on real-time embedded systems (see Literature Reference Nos. 34 and 31).

Existing control software also suffers from a variety of limitations. For example, to date, forward models of human react to perturbations have only been studied for postural stability (see Literature Reference Nos. 18, 19, and 21). Additionally, traditional joint torque control methods based on optimization algorithms (see Literature Reference Nos. 15, and 16) are too computationally intensive to run on real-time embedded systems. Further, leading momentum-based approaches for walking include capture-point methods (see Literature Reference No. 23) and foothold placement control (see Literature Reference No. 26) can be problematic when available footholds are limited.

Actuators used in existing systems also suffer from limitations. Exoskeletons are often heavy and power hungry and encumber movement when in non-assist mode. Further, although Galvanic Vestibular Stimulation (GVS) has been used to enhance postural balance control (see Literature Reference No. 32), it has not been employed to control muscle stimulation in an integrated approach. Instead, the prior art uses functional electro-stimulation (FES), which stimulates activation in muscles; however, FES is only applied to one or two locations limiting its applicability to certain gait pathologies such as drop foot (as described, for example, in Literature Reference No. 42). Finally, training for fall prevention typically uses exercise games (see Literature Reference No. 41), which is preventative but not predictive.

Thus, a continuing need exists for a fall prevention system that is agile (of low power and weight) and that can be easily worn by a user, while still being operable for predicting impending falls by a user and initiating protocols to engage in the prevention of such a fall.

SUMMARY OF INVENTION

Described is a system for gait intervention and fall prevention. In various embodiments, the system includes a body suit having a plurality of distributed sensors and a vestibulo-muscular biostim array. An analytics module is connected with the body suit and sensors. The analytics module is operable for receiving sensor data and, based on the sensor data, analyzing a particular user's gait and predicting falls. A closed-loop biostim control module is also included with the system and, desirably, connected with the suit. The closed-loop biostim control module operable for activating the vestibulo-muscular biostim array to compensate for a risk of a predicted fall.

In another aspect, the vestibulo-muscular biostim array includes multi-site galvanic vestibular stimulation (GVS) effectors proximate a head portion of the suit, whereby the GVS effectors are operable for augmenting a user's vestibular sense.

In yet another aspect, the vestibulo-muscular biostim array also includes functional electrical stimulation (FES) effectors positioned proximate a leg portion of the suit, whereby the FES effectors are operable for stimulating muscles of a user to produce direct control of the user's joint torques.

Additionally, the closed-loop biostim control module includes a biostim controller that applies the torques and balance adjustments to the FES effectors of GVS effectors of the vestibulo-muscular biostim array, in closed-loop control where the adjustments are applied until compensatory effects are achieved.

Further, the body suit is a conformal body suit made of elastic fabric, with the the vestibulo-muscular biostim array being connected with the body suit such that the effectors of the vestibulo-muscular biostim array are positioned against a user's body when wearing the body suit.

In another aspect, the plurality of distributed sensors are selected from a group consisting of electromyography (EMG) sensors, inertial measurement units (IMU) sensors, and ground reaction force (GRF) sensors.

Additionally, in various embodiments, at least some of the sensors are operable for providing biosensor data to the analytics module.

The analytics module includes a musculoskeletal model, a gait analytics module, and a fall prediction module. The gait analytics module updates the musculoskeletal model based on the biosensor data and analyzes gait for a particular user. Further, the fall prediction module runs the updated musculoskeletal model forward in time to determine if fall risk is elevated.

In yet another aspect, the closed-loop biostim control module includes a balance controller that determines joint torques and vestibular balance adjustments required to compensate for a risk of a predicted fall.

In another aspect, the vestibulo-muscular biostim array includes tactile effectors positioned proximate a waste of the suit, whereby the tactile effectors are operable for alerting a user of a predicted fall.

Finally and as noted above, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 5B is a table providing examples of various components as suitable for incorporation into a lightweight and low power soft suit according to various embodiments of the present invention;

FIG. 5C is a table providing examples of various components as suitable for incorporation into a lightweight and low power soft suit according to various embodiments of the present invention;

DETAILED DESCRIPTION

Figure 1:
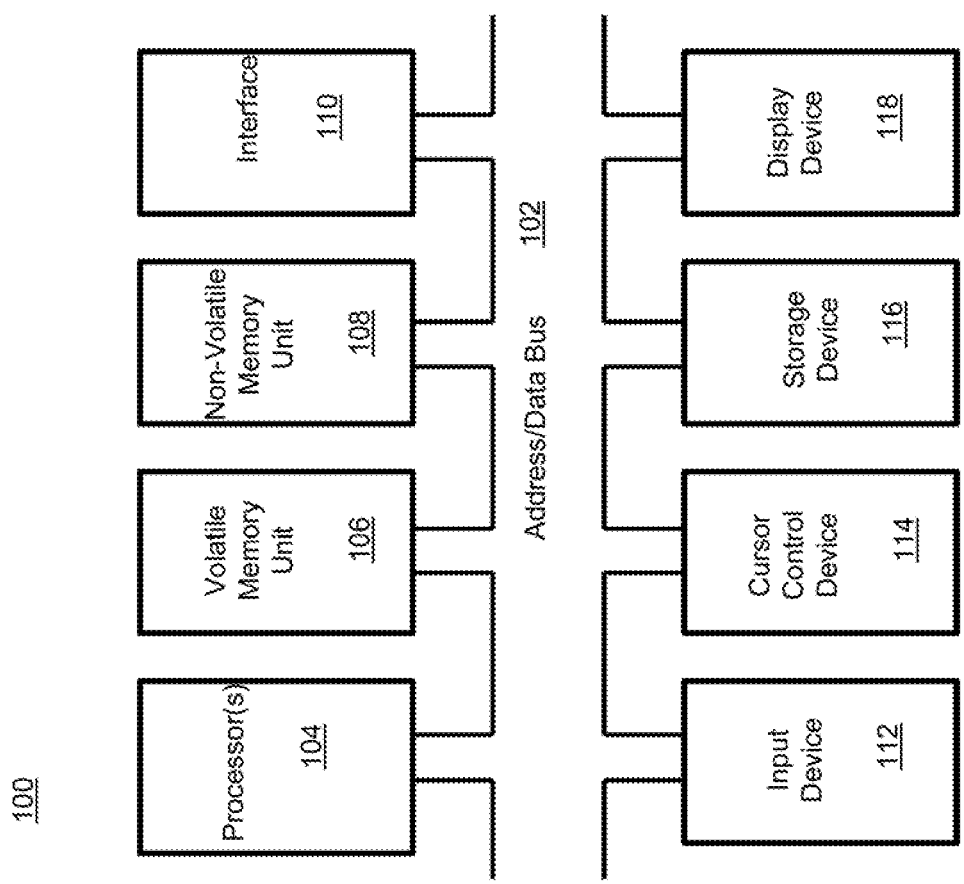
FIG. 1 is a block diagram depicting the components of a system according to various embodiments of the present invention.

The present invention is related to a fall prevention system and, more particularly, to a system incorporating a suit and sensors to predict impending falls by a user and initiate protocols to engage in the prevention of such a fall. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) LIST OF INCORPORATED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number as follows:

1. L. R. Bent, B. J, McFadyen, V. French Merkley, P. M. Kennedy, and J. T. Inglis. Magnitude effects of galvanic vestibular stimulation on the trajectory of human gait. *Neuroscience letters,* 279 (3): 157-160, 2000.
2. C. Boelens, E. E. G. Hekman, and G. J. Verkerke, Risk factors for falls of older citizens. *Technology and Health Care,* pages 1-13, 2013. Doi: 10.3233/THC-130748. URL http://iospress.metapress.com/content/-9180L23KHL7486R0.
3. A. K. Bourke and G. M. Lyons. A threshold-based fall-detection algorithm using a bi-axial gyroscope sensor. *Medical engineering & physics,* 30 (1): 84-90, 2008.
4. V. De Sapio. An approach for goal-oriented neuromuscular control of digital humans in physics-based simulations, *International Journal in Human Factors Modeling and Simulation,* 4 (2): 121-144, 2014.
5. V. De Sapio, J. Warren, O. Khatib, and S. Delp. Simulating the task-level control of human motion: a methodology and framework for implementation. *The Visual Computer,* 21 (5): 289-302, 2005.
6. V. De Sapio, J. Warren, and O. Khatib. Predicting reaching postures using a kinematically constrained shoulder model. In *Advances in robot kinematics,* pages 209-218. Springer, 2006.
7. S. L. Delp, F. C. Anderson, A. S. Arnold, P. Loan, A. Habib, C. T. John, E. Guendelman, and D. G. Thelen. OpenSim: open-source software to create and analyze dynamic simulations of movement. *IEEE Transactions on Biomedical Engineering,* 54 (11): 1940-1950, 2007.
8. F. Englander, T. J. Hodson, and R. A. Terregrossa. Economic dimensions of slip and fall injuries. *Journal of forensic sciences,* 41 (5): 733-746, 1996.
9. J. Fleming and C. Brayne. Inability to get up after falling, subsequent time on floor, and summoning help: prospective cohort study in people over 90. *BMJ: British Medical Journal,* 337, 2008.
10. H. Geyer and H. Herr. A muscle-reflex model that encodes principles of legged mechanics produces human walking dynamics and muscle activities. *IEEE Transactions on Neural Systems and Rehabilitation Engineering,* 18 (3): 263-273, 2010.
11. M. Giftthaler and K. Byl. Increased robustness of humanoid standing balance in the sagittal plane through adaptive joint torque reduction. In *Proceedings of the 2013 IEEE International Conference on Intelligent Robots and Systems,* 2013.
12. M. H. Granat, A. C. B. Ferguson, B. J. Andrews, and M. Delargy. The role of functional electrical stimulation in the rehabilitation of patients with incomplete spinal cord injury-observed benefits during gait studies. *Spinal Cord,* 31 (4): 207-215, 1993.
13. E. E. Hansson and M. Magnusson. Vestibular asymmetry predicts falls among elderly patients with multisensory dizziness. *BMC geriatrics,* 13 (1): 77, 2013.
14. B. Kleiner and D. Cesmeci. D8. 4-foresighted control of active foot prostheses. *Proceedings SENSOR 2011,* pages 669-672, 2011.
15. A. D. Kuo. An optimal control model for analyzing human postural balance. *IEEE Iransactions on Biomedical Engineering,* 42 (1): 87-101, 1995.
16. C. Liu and C. G. Atkeson. Standing balance control using a trajectory library. In *Proceedings of the 2009 IEEE/RSJ International Conference on Intelligent Robots and Systems,* pages 3031-3036. IEEE, 2009.
17. M. Maleševic and S. Hesse. Restoration of gait by functional electrical stimulation in paraplegic patients: a modified programme of treatment. *Spinal Cord,* 33 (3): 126-131, 1995.
18. M. Mansouri and J. A. Reinholt. A platform for dynamic simulation and control of movement based on OpenSim and MATLAB. *Journal of biomechanics,* 45 (8): 1517-1521, 2012.
19. K. Miller. Feedback for the brain and body: A new freely available interface between matlab and opensim. *Biomedical Computation Review,* Summer: 3-4, 2012.
20. A. Murai and K. Yamane. A neuromuscular locomotion controller that realizes human-like responses to unexpected disturbances. In 2011 *IEEE International Conference Robotics and Automation,* pages 1997-2002. IEEE, 2011.
21. S. Piazza, M. Mansouri, D. Torricelli, J. A. Reinbolt, and J. L. Pons. A biomechanical model for the validation of modular control in balance. In *Converging Clinical and Engineering Research on Neurorehabiliation,* pages 815-819. Springer, 2013.
22. J. Piovan and K. Byl. Reachability-based control for the active slip model. *International Journal of Robotics Research,* page Submitted, 2013.
23. J. Pratt, J. Carff, S. Drakunov, and Am. Goswami. Capture point: A step toward humanoid push recovery. In 2006 *6th IEEE-RAS International Conference on Humanoid Robots,* pages 200-207. IEEE, 2006.
24. X. Qu. Effects of cognitive and physical loads on local dynamic stability during gait. *Applied Ergonomics,* 44 (3): 455-458, 2013. ISSN 0003-6870. doi: http://dx-.doi.org/10.1016/j.apergo.2012.10.018. URL http://www.sciencedirect.com/science/article/pii/S0003687012001767.
25. X. Qu and J. C. Yeo. Effects of load carriage and fatigue on gait characteristics. *Journal of biomechanics,* 44 (7): 1259-1263, 2011.
26. M. Raibert, K. Blankespoor, G. Nelson, R. Playter, et al. Bigdog, the rough-terrain quadruped robot. In *Proceedings of the 17th World Congress of the International Federation of Automatic Control,* pages 10823-10825, 2008.
27. J. A. Reinholt, R. T. Haftka, T. L. Chmielewski, and B. J. Fregly. Are patient-specific joint and inertial parameters necessary for accurate inverse dynamics analyses of gait? *IEEE Transactions on Biomedical Engineering,* 54 (5): 782-793, 2007.
28. C. O. Saglam and K. Byl. Switching policies for metastable walking. In *In Proceedings of IEEE Conference on Decision and Control,* 2013. Submitted.
29. M. Sartori, D. G. Lloyd, M. Reggiani, and E. Pagello. A stiff tendon neuromusculoskeletal model of the knee. In 2009 *IEEE Workshop on Advanced Robotics and its Social Impacts,* pages 132-138. IEEE, 2009.
30. M. Sartori, D. G. Lloyd, M. Reggiani, and E. Pagello. Fast operation of anatomical and stiff tendon neuromuscular models in emg-driven modeling. In 2010 *IEEE International Conference on Robotics and Automation,* pages 2228-2234. IEEE, 2010.
31. M. Sartori, M. Reggiani, D. Farina, and D. G. Lloyd. Emg-driven forward-dynamic estimation of muscle force and joint moment about multiple degrees of freedom in the human lower extremity. *PloS one,* 7 (12): e52618, 2012.

32. A. P. Scinicariello, K. Eaton, J. T. Inglis, and J. J. Collins. Enhancing human balance control with galvanic vestibular stimulation. *Biological cybernetics*, 84 (6): 475-480, 2001.
33. L. Seiner, N. S. Bell, M. M. Yore, and P. J. Amoroso. Hospitalizations for fall-related injuries among active-duty army soldiers, 1980-1998. *Work: A Journal of Prevention, Assessment and Rehabilitation*, 18 (2): 161-170, 2002.
34. A. Seth, M. Sherman, J. A. Reinbolt, and S. L. Delp. OpenSim: a musculoskeletal modeling and simulation framework for in silico investigations and exchange. volume 2, pages 212-232. Elsevier, 2011.
35. F. Shuping, M. Canham-Chervak, P. J. Amoroso, and B. H. Jones. Identifying modifiable causes of fall-related injury: An analysis of us army safety data. *Work: A Journal of Prevention Assessment and Rehabilitation*, 33 (1): 23-34, 2009.
36. Yousuke Suzuki, Takayuki Tanaka, Shun'ichi Kaneko, Shunji Moromugi, and Maria Q Feng. Soft sensor suits as man-machine interface for wearable power amplifier. In *Systems, Man and Cybernetics, 2005 IEEE International Conference on*, volume 2, pages 1680-1685. IEEE, 2005.
37. W. Tao, T. Liu, R. Zheng, and H. Feng. Gait analysis using wearable sensors. *Sensors*, 12 (2): 2255-2283, 2012.
38. D. G. Thelen and F. C. Anderson. Using computed muscle control to generate forward dynamic simulations of human walking from experimental data. *Journal of Biomechanics*, 39 (6): 1107-1115, 2006.
39. D. G. Thelen, F. C. Anderson, and S. L. Delp. Generating dynamic simulations of movement using computed muscle control. *Journal of Biomechanics*, 36 (3): 321-328, 2003.
40. K. Tsukada and M. Yasumura "Activebelt: Belt-type wearable tactile display for directional navigation." UbiComp 2004: Ubiquitous Computing. Springer Berlin Heidelberg, 2004. 384-399.
41. M. Van Diest, C. J. C. Lamoth, J. Stegenga, G. J. Verkerke, and K. Postema. Exergaming for balance training of elderly: state of the art and future developments. *Journal of neuroengineering and rehabilitation*, 10 (1): 101, 2013.
42. R. van Swigchem, J. Vloothuis, J. den Boer, V. Weerdesteyn, and A. C H. Geurts. Is transcutaneous peroneal stimulation beneficial to patients with chronic stroke using an ankle-foot orthosis? A within-subjects study of patients' satisfaction, walking speed and physical activity level. *Journal of Rehabilitation Medicine*, 42 (2): 117-121, 2010.
43. Q. Zhang, M. Hayashibe, and C. Azevedo-Coste. Evoked electromyography-based closed-loop torque control in functional electrical stimulation. *IEEE Transactions on Biomedical Engineering*, 60: 2299-2307, 2013.
44. Y. Zigel, D. Litvak, and I. Gannot. A method for automatic fall detection of elderly people using floor vibrations and sound—proof of concept on human mimicking doll falls. *IEEE Transactions on Biomedical Engineering*, 56 (12): 2858-2867, 2009.

(2) PRINCIPAL ASPECTS

Various embodiments of the invention include three "principal" aspects. The first is a system for assistive gait intervention and fall prevention. The system is typically in the form of a computer system operating software or in the form of a "hard-coded" instruction set. This system may be incorporated into a wide variety of devices that provide different functionalities. For example and in various embodiments, the system is incorporated into a suit with sensors, effectors, and various components having the features and functionalities as described herein. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., the computer system 100 portion) of the present invention is provided in FIG. 1. As described above and in further detail below, the computer system 100 can be incorporated into a suit with sensors and various components and is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device (or in addition to), such as any suitable input device, such a microphone for voice commences and/or a sensor suite. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
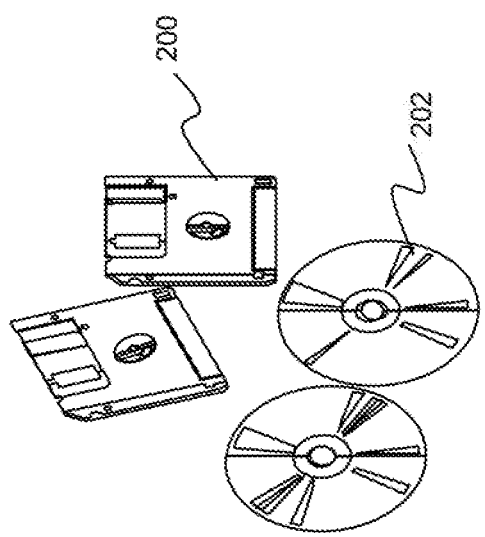
FIG. 2 is an illustration of a computer program product embodying an aspect of the present invention.

An illustrative diagram of a computer program product (i.e., storage device) embodying an aspect of the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

Figure 3:
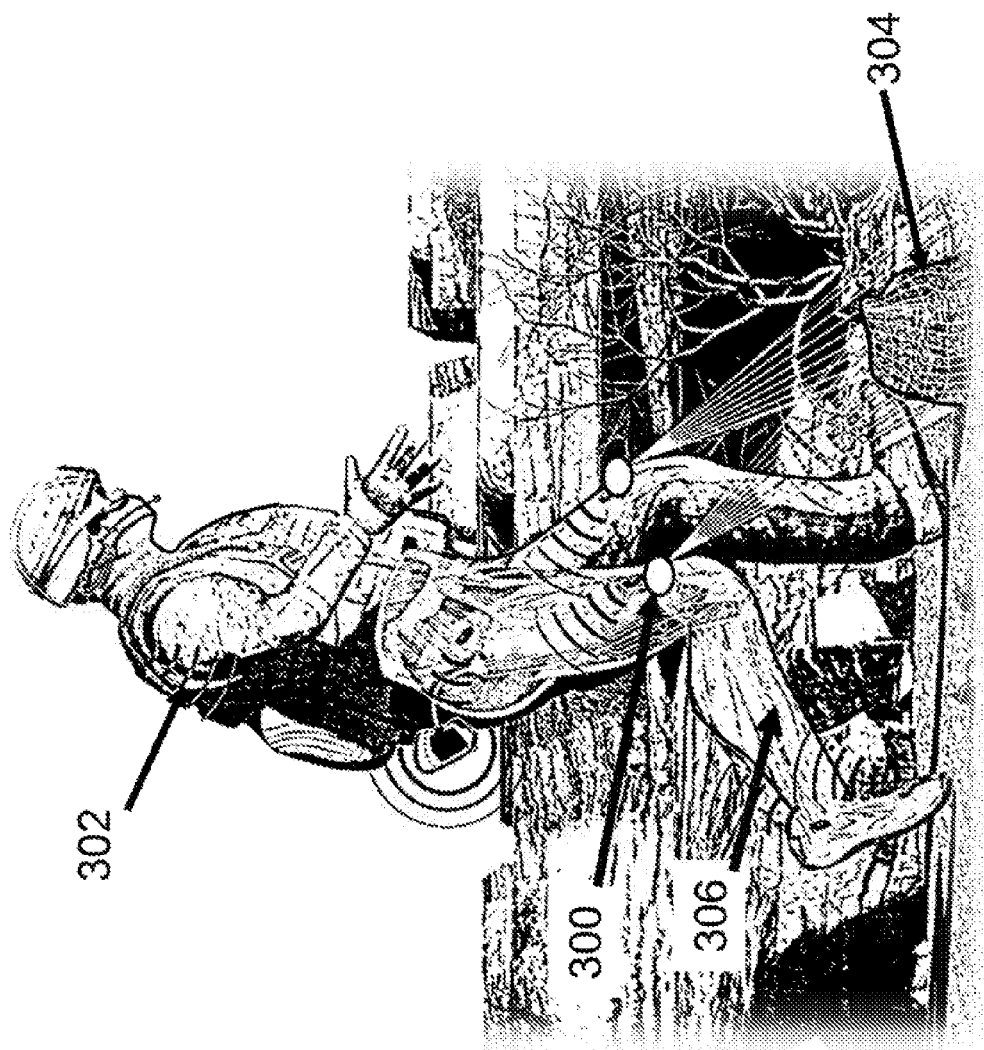
FIG. 3 is an illustration depicting the system according to various embodiments being incorporated into a soft suit and worn by a user.

This disclosure provides a new approach to enhance gait kinematics while predicting and preventing falls. As shown in FIG. 3, with lightweight distributed sensors 300 (e.g. more than one hundred sensors) integrated into a soft, stretchable, full-body suit 302, the system is able to predict impending falls caused by extrinsic factors (environmental) 304 like tripping and intrinsic factors (physiological) such as balance and coordination. Principal among these factors are balance (including dizziness/vertigo), muscle coordination, and strength. In the event of a predicted fall, integrated haptics alert the user to consciously engage in the prevention of a fall. Simultaneously, the invention proactively corrects muscle imbalances, stabilizes gait, and mitigates the risk of a fall with a complementary blend of effectors 306 that synergistically enhance muscle activations and optimize the sense of balance, with its control system directing a corrective pattern of haptics and electrostimulation. The system monitors the results in a tight feedback loop, adjusting parameters in real time. The coordination of functional electrical stimulation (FES) to control muscle activations, and galvanic vestibular stimulation (GV) to control balance is a new and unique concept as provided by this disclosure.

The state of the art detects falls by means of accelerometers, and uses stiff, weight-bearing exoskeletons to stop a fall. Alternatively, the system described herein is designed into a lightweight, low power, soft, conformal suit. This sets it apart from the prior art as exoskeletons are uncomfortable, expensive, and impede the mobility of the wearer if they run out of power. With such a bulky, stiff exoskeleton, prior art solutions can wait until a fall is happening and then detect it and use the stiff exoskeleton to stop it. The system described herein uses accurate early prediction, not detection, and uses earlier mitigation to help remediate the gait by means of functional electro-stimulation (FES) of the muscles, as well as galvanic vestibular stimulation to control the balance. To be fully effective and ergonomically wearable, environmental and physiological sensing and electro-actuation must also be flexible, and have low size, weight, and power, which the approach herein improves over state of the art exoskeletons. The system can be provided as a companion or replacement to high-priced personalized physical therapy available for top athletes or used by elderly, soldiers, or others at risk of a fall.

(4) SPECIFIC DETAILS OF VARIOUS EMBODIMENTS

Figure 4:
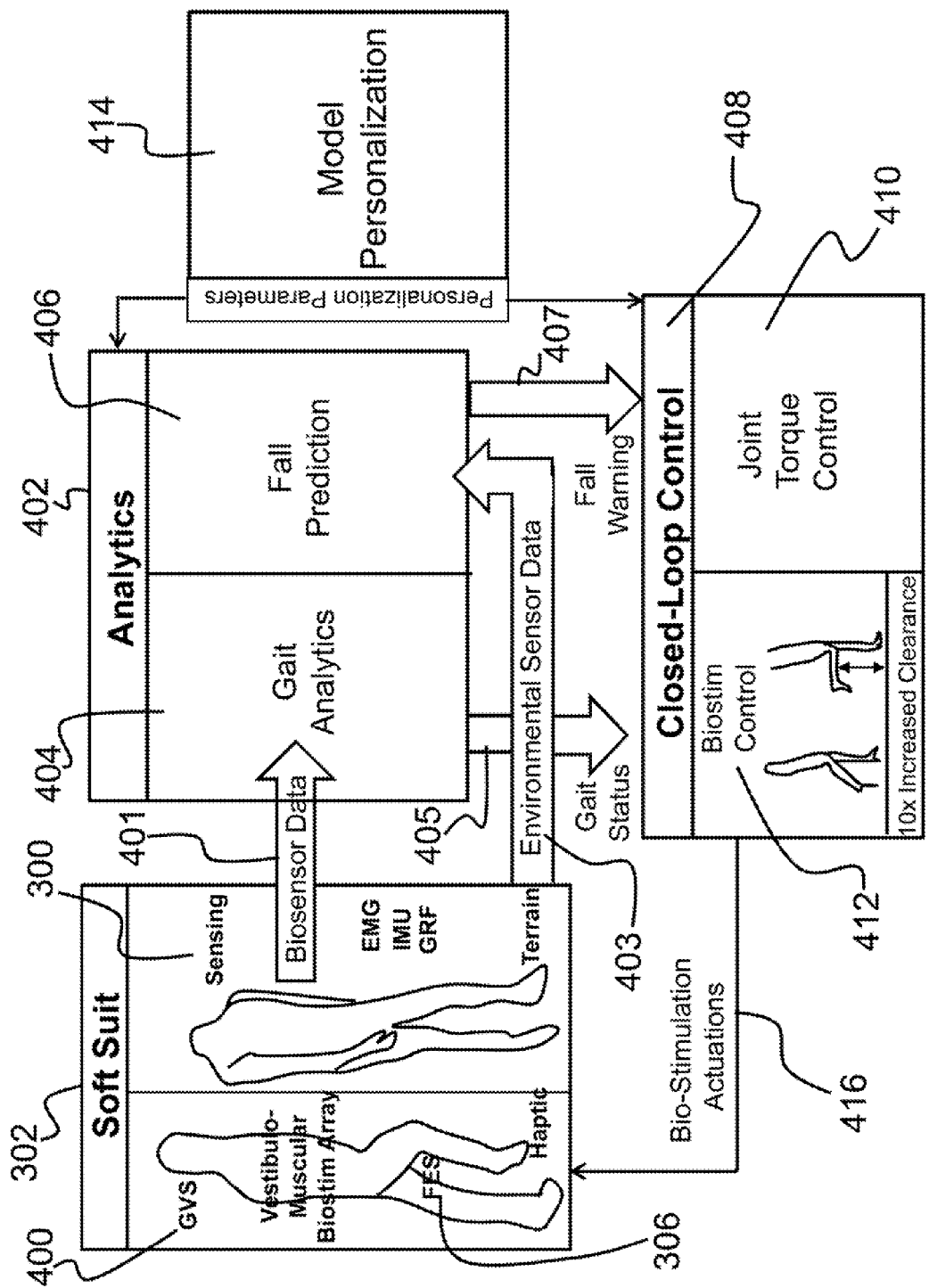
FIG. 4 is a high-level system diagram, illustrating modules of the system according to various embodiments.

As noted above, this disclosure provides a system for assistive gait intervention and fall prevention. FIG. 4 provides an illustrative flow chart depicting the various components of the system. For example, the system described herein includes a soft suit 302. The soft suit 302 is a garment or article of clothing (e.g., bodysuit, jacket, vest, pants, etc.) that is pliable and light weight (e.g., less than four kilograms). The soft suit 302 incorporates a variety of distributed sensors 300 and the vestibulo-muscular biostim array 400. The sensors 300 provide biosensor data 401 and environmental sensor data 403 to a software analytics module 402. The software analytics module 402 runs on an embedded processor (or wirelessly connected remote processor), analyzing gait (via a gait analytics module 404) and predicting falls (via a fall prediction module 406) using a musculoskeletal model 414 running on a real-time physics based simulator. The musculoskeletal model 414 is personalized offline and incorporated into the analytics module 402. Both gait status 405 and a fall warning 407 (i.e., if a fall is predicted) are provided to the closed-loop biostim control module 408. The closed-loop biostim control module 408 includes a biostim controller 412 and a joint torque controller 410 (balance control) that computes joint torques required to compensate for fall risk, and sends closed-loop control signals (i.e., bio-stimulation actuations 416) to the vestibulo-muscular biostim array 400. The vestibulo-muscular biostim array 400 includes the effectors 306 in the soft suit 302 which are activated to provide gait enhancement and fall prevention.

Figure 5A:
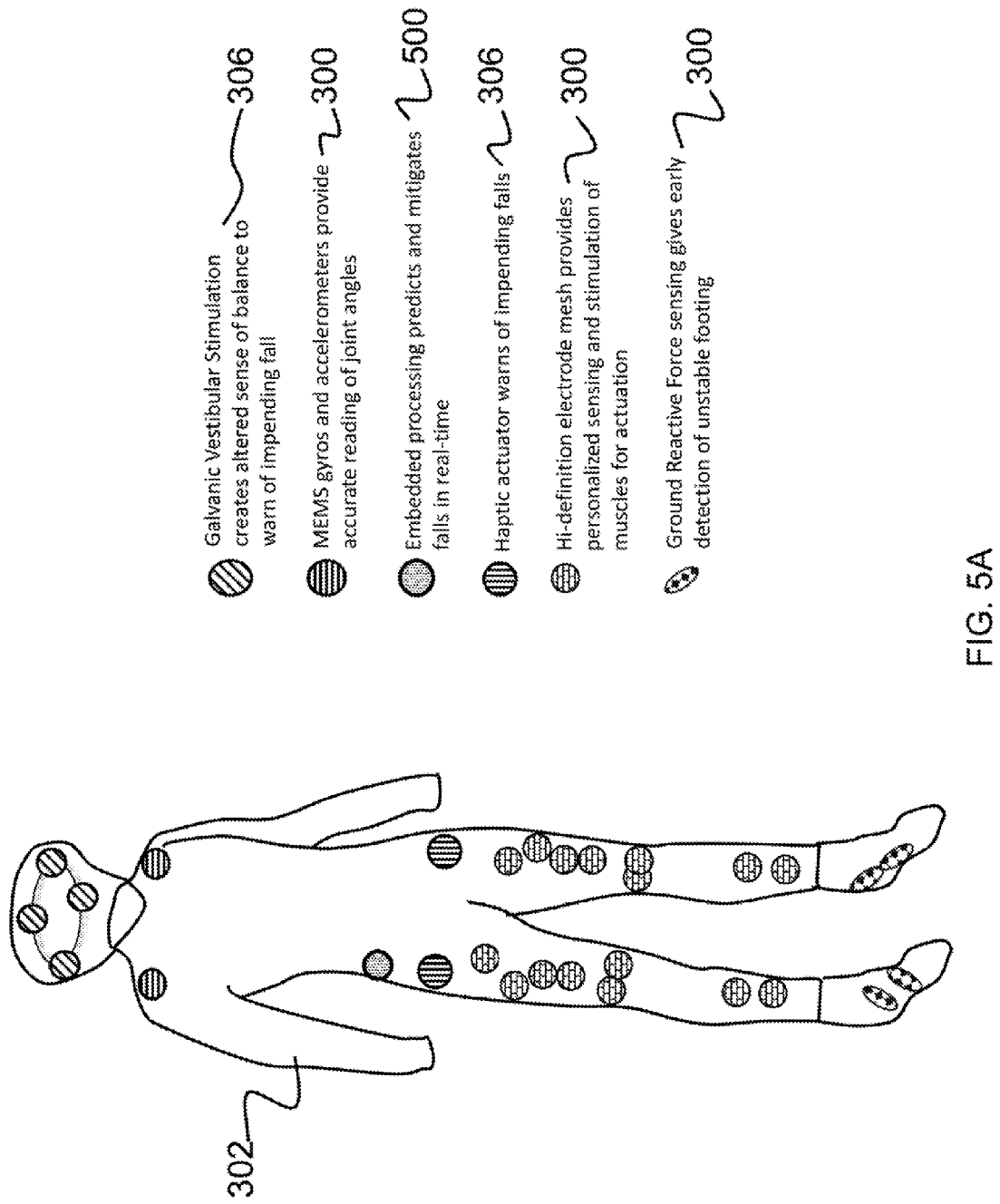
FIG. 5A is an illustration of a soft suit integrating the major subsystems to perform sensing, processing, and actuation.

As shown in the suit system architecture diagram of FIG. 5A, the soft suit 302 system incorporates a number of distributed sensors 300 and effectors 306 located on the head, body, and feet, with embedded processing 500 and power on board the suit 302. Non-limiting examples of such distributed sensors include Electromyography (EMG) sensors, Inertial Measurement Unit (IMU) sensors, and Ground Reaction Force (GRF) sensors. Further, non-limiting examples of such effectors include Functional Electrical Stimulation (FES) effectors, Galvanic Vestibular Stimulation (GVS) effectors, and haptic stimulators. For further specific examples, FIGS. 5B and 5C provide tables describing non-limiting examples of various components as suitable for incorporation into the lightweight and low power soft suit as described herein.

Figure 6:
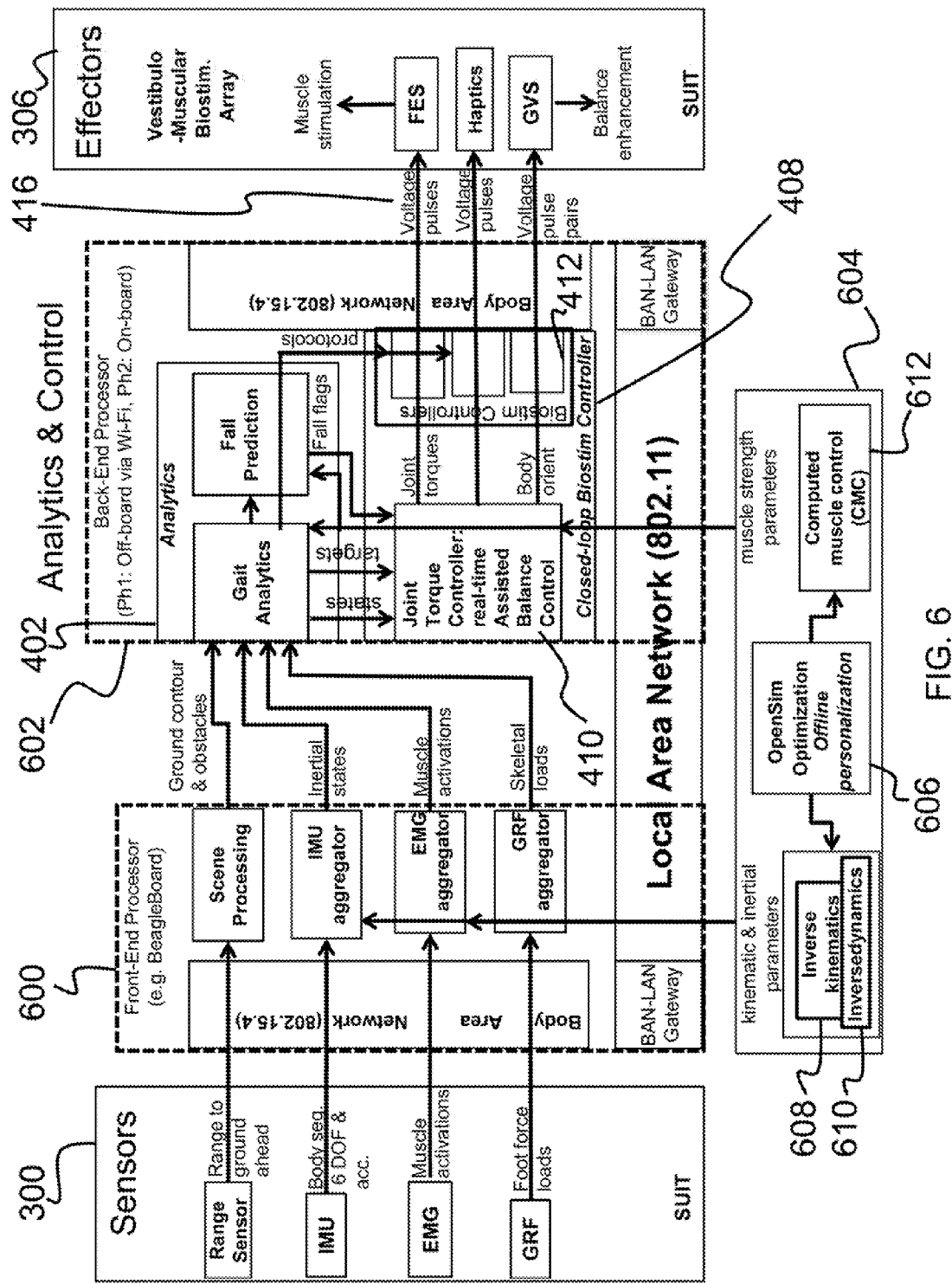
FIG. 6 is diagram depicting process flow and modules according to various embodiments of the present invention.

For further understanding, FIG. 6 diagrams the modules necessary to process the sensor 300 inputs on the front-end processor 600 and produce bio-stimulation actuations 416 from control software as implemented on the back-end processor 602 (by the analytics module 402 and closed-loop biostim control module 408), as well as the basic connectivity. IMU, EMG, and GRF sensors are example sensors 300 that constitute an artificial vestibular and proprioceptive system that provides biomechanical state to the analytics module 402. IMUs detect inertial characteristics, joint and limb kinematics; EMG detects muscle exertion; and GRF detects the center of pressure and ground reaction forces during foot placement. The bio-stimulation actuations 416 are provided to the effectors 306 that provide an array of biostimulation.

The effectors 306 are implemented as a Vestibulo-Muscular Biostim Array, which effects three types of biostimulation. Tactile effectors on the waist will alert users of imminent falls. A non-limiting example of such a tactile (haptic) effector includes that as disclosed in "Activebelt: Belt-type wearable tactile display for directional navigation" (see Literature Reference No. 40). Functional Electrical Stimulation (FES) effectors stimulate muscles to produce direct control of the user's joint torques. Multi-site Galvanic Vestibular Stimulation (GVS) effectors augment the user's vestibular sense to increase postural stability, balance, and suppress muscle tremors. The 4-electrode GVS system augments the user's balance to match vestibular perception to the 3-degree of freedom rotational axes of the users' motions and positions acquired from the inertial sensors. This system can mitigate the loss of vestibular sensation often attributed as a leading cause of falls in the elderly (see, for example, Literature Reference No. 13).

As noted above, the suit's Vestibulo-Muscular Biostim Array effectors are controlled by two key software modules (the analytics module 402 and the closed-loop biostim control module 408). Control signal outputs are based on sensor inputs recording the user's gait, balance, and muscle coordination, and from the predicted stability using the individualized musculoskeletal model. A generic musculoskeletal model is tuned offline to provide accurate subject-specific state estimation and prediction, resulting in a dataset that is used online by the analytics 402 and control 408 modules.

The offline personalization module 604 is shown in FIG. 6. Based on the results of physiological tests on the subject, an inverse kinematics optimization 608 determines model kinematics that best match the experimentally measured motion. Then inverse dynamics 610 determines residual forces and torques (e.g., additional generalized forces necessary to balance the equations of motion) representing errors in the experimental measurements (e.g., motion and ground reaction forces), kinematics, and model parameters (e.g., body segment lengths, masses, etc.). These residual forces and torques are minimized by adjusting design variables, including body segment lengths, joint definitions, and inertial properties of body segments, with the constraints that total body mass and height match the physical exam values.

Figure 7:
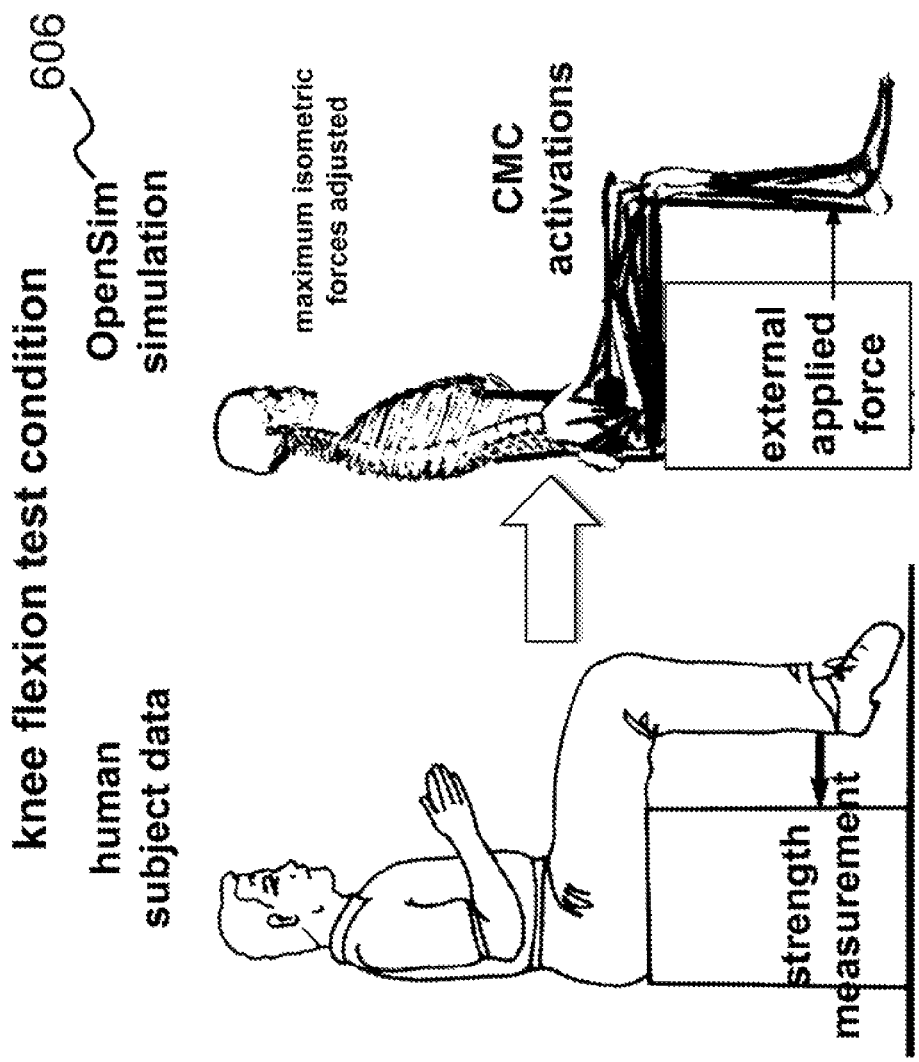
FIG. 7 depicts an example test procedure as used to personalize the musculoskeletal model.

To tune the muscle strength parameters (e.g., maximum isometric strength, etc.), the subject performs a set of isometric strength tests (an example of which is illustrated in FIG. 7, such as knee flexion/extension, etc.), and each test condition is replicated in simulation 606 (e.g., OpenSim) using the musculoskeletal model updated with the subject-specific inertial properties described above. The test procedure is used to personalize the musculoskeletal model, so that subsequently it can accurately judge deviations from optimum performance.

The computed muscle control (CMC) module 612 will then generate muscle activation patterns that maintain the isometric test posture while resisting the force/moment data associated with the isometric strength measurement for that test condition. This procedure is described in U.S. patent application Ser. No. 14/502,478, filed on Sep. 30, 2014 and entitled, "Method and System for Tuning a Musculoskeletal Model," the entirety of which is hereby incorporated by reference as though fully set forth herein. Maximum isometric forces in the muscles are adjusted and then CMC 612 is run until the maximum isometric forces are consistent with the experimental strength data for the subject.

Figure 8:
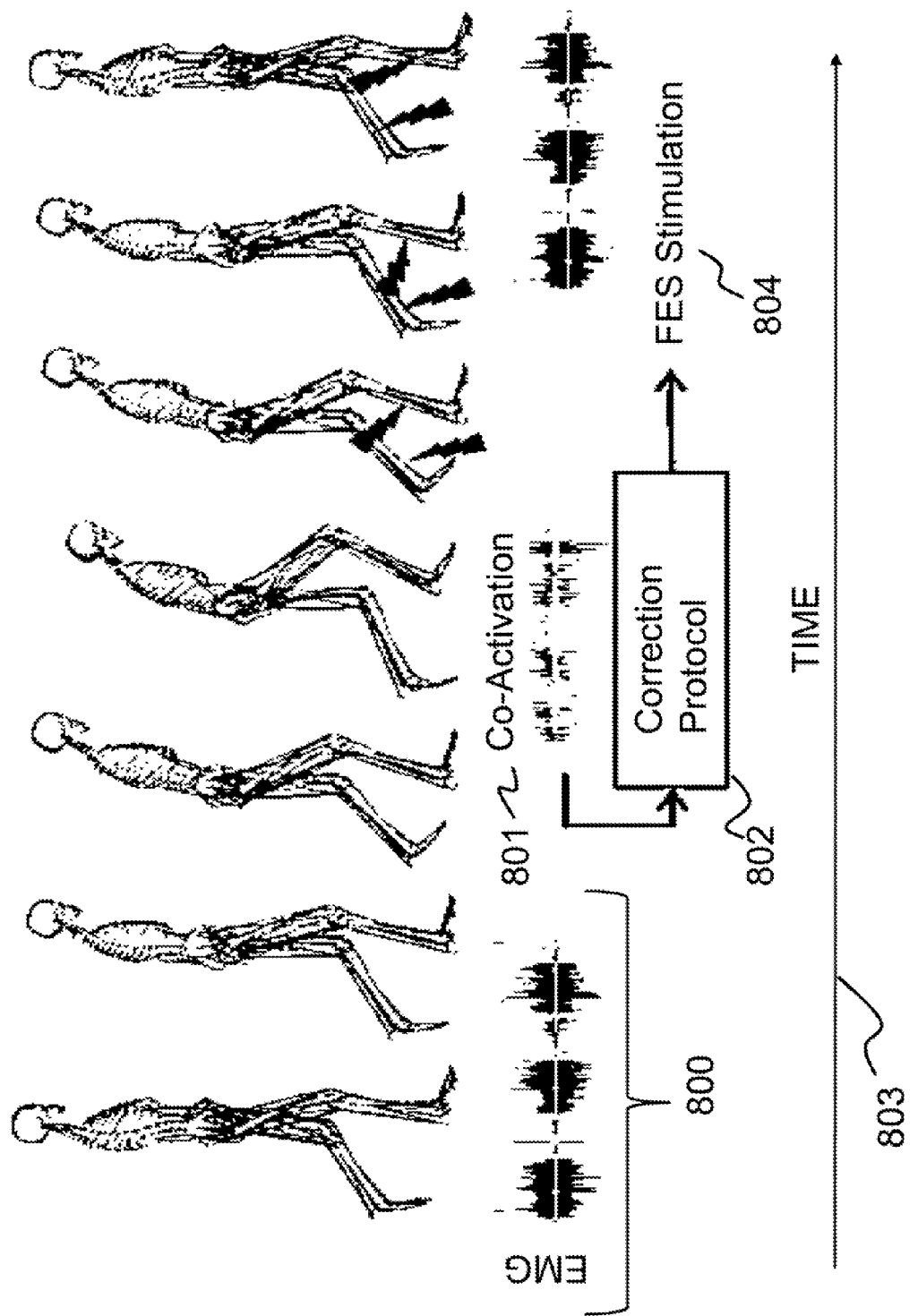
FIG. 8 is an illustration depicting error in correct gait as being recognized by muscle activity of antagonistic muscles that begin to show signs of co-activation during fatigue, and that are corrected by stimulating muscles to improve activation firing patterns.

As noted above, the analytics module 402 performs gait analytics and predicts falls using the gait analytics module 404 and fall prediction module 406, respectively. With respect to gait analytics, the analytics module 402 must run in a real-time environment; thus, OpenSim's CMC-like control algorithms are employed using simplified assumptions on the muscles (see, for example, Literature Reference Nos. 5, 29, and 30. A pilot study of the CMC control on muscles was performed (see Literature Reference No. 4) using a stiff-tendon assumption to vastly increase the speed of performing CMC computations to the level of real-time performance of physics engines for video games. Assuming stiff tendons and instantaneous activation dynamics eliminated the first order differential equations associated with the traditional Hill-type model. Furthermore, fast inverse dynamics for this approach can estimate muscle activations and forces directly from kinematic state and state derivatives (see Literature Reference no. 4). For example and as shown in FIG. 8, gait analytics 404 utilizes EMG sensors (which generates the relevant EMG patterns 800) to assess changes to muscle activation patterns over time 803 that may cause falls. As a non-limiting example, coordination between muscles will be monitored for patterns indicating fatigue or co-activation 801 of antagonistic muscles, which occurs commonly in the elderly. Specifically, a decrease in EMG median power frequency over time is associated with fatigue. This decrease can be detected by processing the raw EMG signal and a fatigue threshold can be set using this metric. Another metric indicating fatigue is joint angle variability, which can be detected by processing the IMU signal. Co-activation of antagonistic muscles can similarly be detected by tracking agonist-antagonist pairs of muscles on EMG and identifying in-phase patterns in the EMG signal. Precise thresholds for these metrics can be established during a training phase with the system by evaluating what level precipitates a fall for a given individual. Error in correct gait recognized by muscle activity of antagonistic muscles that begin to show signs of co-activation 801 during fatigue trigger a correction/stimulation protocol 802 to correct the gait by stimulating muscles (e.g., FES stimulation 804) to improve activation firing patterns. In other words, when the model identifies anomalies in EMG (as well as IMU) patterns associated with established thresholds for the individual 800, the closed-loop biostim control module will determine stimulation protocols 802 to restore normal muscle activation patterns. The control protocol for the closed-loop biostim is described in further detail below with respect to FIG. 9. Exemplary muscles that may be activated may include individual or pairs of muscle groups in a person's buttocks, thigh, knee, calf, and/or foot.

In addition to gait analytics, low-level postural stability and fall prediction analysis are performed by modeling the lower extremity muscles under reflex control. The fall prediction module runs the updated musculoskeletal model forward in time to see if fall risk is elevated. One embodiment adapts a stretch-reflex controller a demonstrated in Literature Reference Nos. 10 and 20. The stretch-reflex controller is dependent on static and dynamic control parameters and a general reflex gain, and is used to manage muscle response to postural perturbations. The general reflex gain adjusts the sensitivity of the stretch-reflex, and is incorporated with the length and velocity control parameters to define each muscle excitation through time.

As noted above, the closed-loop biostim control module 408 includes two sub-modules, a biostim controller 412 and a joint torque controller 410 (i.e., Real-time Assisted Balance Control (rtABC) or balance controller). The joint torque controller 410 (also referred to as the balance control) involves the generation of compensation to actively enhance gait, prevent falls, and restore postural stability to the subject through control of joint torques across multiple joints. Given the required compensation, the biostim controller 412 plans and directs a pattern of biostimulation to haptics, the vestibular system, and the muscles, which will be applied by the Vestibulo-Muscular Biostim Array in the suit.

The joint torque controller 410 leverages prior art in torque-based control of bipedal systems (see Literature Reference Nos. 10, 47, and 54). To convert torque-based control inputs to FES patterns, the system evokes electromyography-based closed-loop torque control using FES (see, for example, Literature Reference No. 43). By using estimates of the subject's joint moments during the gait cycle, (based on sensed data and inverse dynamics performed by the gait analytics subsystem), as well as EMG, a torque control feedback loop is employed to generate FES inputs to achieve desired compensatory joint torques. In addition to FES, the complementary stimulation input, GVS, is also integrated to proactively stabilize the subject using vestibular rather than musculoskeletal inputs. See FIG. 6 for a notional diagram of the relevant connections.

Figure 9:
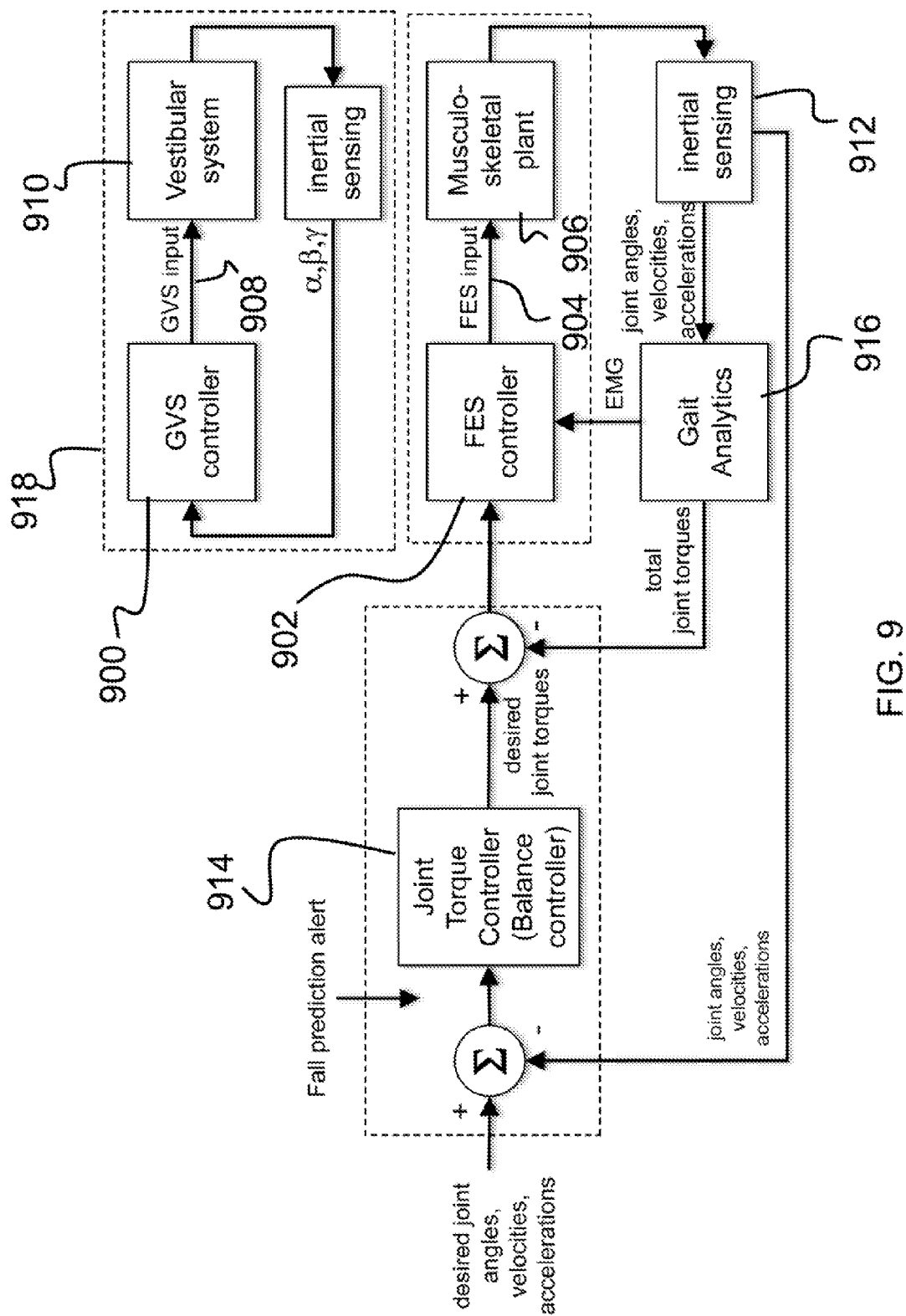
FIG. 9 is a high-level control system diagram of the closed-loop biostim control module according to various embodiments of the present invention.

For further understanding, FIG. 9 depicts a high-level control system diagram of the closed-loop biostim control module. The diagram shows the coordinated balance using a GVS controller 900 (to activate GVS), and muscle activations using the FES controller 902 (to activate FES).

In the embodiment as depicted in FIG. 9, balance is controlled by two independent but complementary processes running in parallel; one involving an FES control input 904 into the musculoskeletal system 906 and the other involving a GVS control input 908 into the vestibular system 910. The FES control input 904 directly modifies muscle action and the GVS control input 908 modifies vestibular perception, allowing the body's own motor control system to modify muscle action.

In the FES case, desired joint angles, velocities, and accelerations (all as associated with stable gait) are compared to the subject's actual values measured by the inertial sensing block 912. For example, measurements for the above variables may be taken during a leg swing phase, such as at the beginning, at a midpoint location within the swing, or near the termination of the swing. Other phases that might be points for measurement may include a leg plant phase. The measurements may be taken during the stride, stand, or seated phase. The measurements may also be characterized by groups of variables. For example, measurements may be taken of muscle output, limb velocity, or limb acceleration at a maximum or minimum swing angle for an individual leg, an angle separation of both legs.

The error between the desired joint values, necessary for stable gait, and the actual values is input into the balance controller 914 which determines the desired total joint torques needed to compensate for the error and maintain stable gait. The difference between the desired joint torques and the actual joint torques, estimated by the gait analytics block 916 using the inertial sensing data, provides an input to the FES controller 902, Based on the joint torque error the FES controller 902 determines the pattern and level of stimulation to the muscles that is required to supplement the actual torques generated by the muscles so that the desired total torques can be achieved. This targeted stimulation results in an FES augmented musculoskeletal state that is continuously monitored by the inertial sensing 912 system as the control loop continues to execute.

The GVS compensation module 918 runs in parallel to provide additional compensatory input; this time to the vestibular system 910 rather than the musculoskeletal system 906. As the inertial sensing block 912 measures degeneration in balance (measured by the postural angles of the body) a signal is sent to the GVS controller 900 which determines the pattern and level of corrective stimulation to provide to the vestibular system 910. For example, if the subject's posture is progressively inclining forward, the GVS controller 900 would send a signal to the vestibular system 910 to amplify the subject's vestibular perception that he/she is falling forward. The subject's own postural control system would then correct for the postural degeneration through corrective muscle activation. Exemplary angles at which the GVS controller 900 may activate may be greater than 20, 30, 40, 50, or 60 degrees away from vertical.

In summary, the suit system invention integrates a variety of sensors and actuators into a conformal, lightweight (<4 kg) soft suit, with low power requirements (<12 W when not considering regenerative power insoles or other power generators). GVS will augment balance for short-term fall mitigation based on low latency sensors while FES will remediate longer term gait issues (see FIG. 4). Haptic warnings provide feedback to the user to correct deficiencies in balance and gait.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for gait intervention and fall prevention, the system comprising:
   a body suit having a plurality of distributed sensors and a vestibulo-muscular biostim array;
   an analytics module connected with the body suit and sensors, the analytics module operable for receiving sensor data and, based on the sensor data, analyzing a particular user's gait and predicting falls; and
   a closed-loop biostim control module operable for activating the vestibulo-muscular biostim array to compensate for a risk of a predicted fall, wherein the closed-loop biostim control module includes a balance controller that determines joint torques and vestibular balance adjustments required to compensate for a risk of a predicted fall.

2. The system as set forth in claim 1, wherein the vestibulo-muscular biostim array includes multi-site galvanic vestibular stimulation (GVS) effectors proximate a head portion of the suit, whereby the GVS effectors are operable for augmenting a user's vestibular sense;
   wherein the vestibulo-muscular biostim array also includes functional electrical stimulation (FES) effectors positioned proximate a leg portion of the suit, whereby the FES effectors are operable for stimulating muscles of a user to produce direct control of the user's joint torques;
   wherein the closed-loop biostim control module includes a biostim controller that applies the torques and balance adjustments to the FES effectors of GVS effectors of the vestibulo-muscular biostim array, in closed-loop control where the adjustments are applied until compensatory effects are achieved;
   wherein the body suit is a conformal body suit made of elastic fabric, with the vestibulo-muscular biostim array being connected with the body suit such that the effectors of the vestibulo-muscular biostim array are positioned against a user's body when wearing the body suit;
   wherein the plurality of distributed sensors are selected from a group consisting of electromyography (EMG) sensors, inertial measurement units (IMU) sensors, and ground reaction force (GRF) sensors;
   wherein the sensors are operable for providing biosensor data to the analytics module;
   wherein the analytics module includes a musculoskeletal model, a gait analytics module, and a fall prediction module, wherein the gait analytics module updates the musculoskeletal model based on the biosensor data and analyzes gait for a particular user, and wherein the fall prediction module runs the updated musculoskeletal model forward in time to determine if fall risk is elevated;
   and
   wherein the vestibulo-muscular biostim array includes tactile effectors positioned proximate a waist of the suit, whereby the tactile effectors are operable for alerting a user of a predicted fall.

3. The system as set forth in claim 1, wherein the vestibulo-muscular biostim array includes multi-site galvanic vestibular stimulation (GVS) effectors proximate a head portion of the suit, whereby the GVS effectors are operable for augmenting a user's vestibular sense.

4. The system as set forth in claim 1, wherein the vestibulo-muscular biostim array includes functional electrical stimulation (FES) effectors positioned proximate a leg portion of the suit, whereby the FES effectors are operable for stimulating muscles of a user to produce direct control of the user's joint torques.

5. The system as set forth in claim 1, wherein the vestibulo-muscular biostim array includes multi-site galvanic vestibular stimulation (GVS) effectors proximate a head portion of the suit, and wherein the vestibulo-muscular biostim array includes functional electrical stimulation (FES) effectors positioned proximate a leg portion of the suit, and wherein the closed-loop biostim control module includes a biostim controller that applies the torques and balance adjustments to the FES effectors of GVS effectors of the vestibulo-muscular biostim array, in closed-loop control where the adjustments are applied until compensatory effects are achieved.

6. The system as set forth in claim 1, wherein the vestibulo-muscular biostim array includes a plurality of distributed effectors, and wherein the body suit is a conformal body suit made of elastic fabric, with the vestibulo-muscular biostim array being connected with the body suit such that the effectors of the vestibulo-muscular biostim array are positioned against a user's body when wearing the body suit.

7. The system as set forth in claim 1, wherein the plurality of distributed sensors are selected from a group consisting of electromyography (EMG) sensors, inertial measurement units (IMU) sensors, and ground reaction force (GRF) sensors.

8. The system as set forth in claim 1, wherein the sensors are operable for providing biosensor data to the analytics module.

9. The system as set forth in claim 1, wherein the vestibulo-muscular biostim array includes a plurality of distributed effectors.

10. The system as set forth in claim 1, wherein the sensors are operable for providing biosensor data to the analytics module and wherein the analytics module includes a musculoskeletal model, a gait analytics module, and a fall prediction module, wherein the gait analytics module updates the musculoskeletal model based on the biosensor data and analyzes gait for a particular user, and wherein the fall prediction module runs the updated musculoskeletal model forward in time to determine if fall risk is elevated.

11. The system as set forth in claim 1, wherein the vestibulo-muscular biostim array includes tactile effectors positioned proximate a waist of the suit, whereby the tactile effectors are operable for alerting a user of a predicted fall.

12. A computer program product for gait intervention and fall prevention, the system comprising:
 a non-transitory computer-readable medium having executable instructions encoded thereon, such that upon execution of the instructions by one or more processors, the one or more processors perform operations of:
  receiving, with an analytics module, sensor data from a plurality of sensors distributed about a body suit and, based on the sensor data, analyzing a particular user's gait and predicting falls;
  utilizing a balance controller to determine joint torques and vestibular balance adjustments required to compensate for a risk of a predicted fall; and
  activating, with a closed-loop biostim control module, a vestibulo-muscular biostim array distributed about the body suite to compensate for a risk of a predicted fall.

13. The computer program product as set forth in claim 12, wherein the sensors are operable for providing biosensor data to the analytics module and wherein the analytics module includes a musculoskeletal model, a gait analytics module, and a fall prediction module, wherein the gait analytics module updates the musculoskeletal model based on the biosensor data and analyzes gait for a particular user, and wherein the fall prediction module runs the updated musculoskeletal model forward in time to determine if fall risk is elevated.

14. The computer program product as set forth in claim 12, wherein the vestibulo-muscular biostim array includes tactile effectors positioned proximate a waist of the suit, and further comprising instructions for causing the tactile effectors to alert a user of a predicted fall.

15. A computer implemented method for gait intervention and fall prevention, the method comprising an act of causing one or more processors to execute instructions encoded on a non-transitory computer readable medium, such that upon execution of the instructions, the one or more processors perform operations of:
 receiving, with an analytics module, sensor data from a plurality of sensors distributed about a body suit and, based on the sensor data, analyzing a particular user's gait and predicting falls;
 utilizing a balance controller to determine joint torques and vestibular balance adjustments required to compensate for a risk of a predicted fall; and
 activating, with a closed-loop biostim control module, a vestibulo-muscular biostim array distributed about the body suit to compensate for a risk of a predicted fall.

16. The computer implemented method as set forth in claim 15, wherein the sensors are operable for providing biosensor data to the analytics module and wherein the analytics module includes a musculoskeletal model, a gait analytics module, and a fall prediction module, wherein the gait analytics module updates the musculoskeletal model based on the biosensor data and analyzes gait for a particular user, and wherein the fall prediction module runs the updated musculoskeletal model forward in time to determine if fall risk is elevated.

17. The computer program product as set forth in claim 15, wherein the vestibulo-muscular biostim array includes tactile effectors positioned proximate a waist of the suit, and further comprising an operation of causing the tactile effectors to alert a user of a predicted fall.

* * * * *